United States Patent [19]

Glomstead

[11] Patent Number: 4,747,399

[45] Date of Patent: May 31, 1988

[54] MEDICAL APPLIANCE HAVING AUXILIARY BELT TO PROVIDE ADJUSTABLE LENGTH RANGES

[76] Inventor: Roger R. Glomstead, 1390 Kirkway, Bloomfield Hills, Mich. 48013

[21] Appl. No.: 44,993

[22] Filed: Apr. 30, 1987

[51] Int. Cl.[4] .......................... A61F 5/04; A61F 5/02

[52] U.S. Cl. ........................................ 128/75; 128/78; 128/DIG. 23; 2/DIG. 6; 2/339; 450/135

[58] Field of Search ......... 128/75, 78, 84 R, DIG. 23; 2/339, 338, DIG. 6; 450/135, 133, 134, 140, 149

[56] References Cited

U.S. PATENT DOCUMENTS

| | | | |
|---|---|---|---|
| 1,267,657 | 5/1918 | Grace | 450/18 |
| 1,928,101 | 9/1933 | Grinager et al. | 33/15 |
| 3,115,879 | 12/1963 | Kaplan | 450/134 |
| 3,434,469 | 3/1969 | Swift | 128/87 R |
| 3,598,114 | 8/1971 | Lewis | 128/78 |
| 3,752,163 | 8/1973 | Kaplan | 450/117 |
| 3,812,862 | 5/1974 | Bernstein | 128/78 |
| 3,902,503 | 9/1975 | Gaylord, Jr. | 128/78 |
| 4,497,069 | 2/1985 | Braunhat | 2/DIG. 6 |

FOREIGN PATENT DOCUMENTS

| | | | |
|---|---|---|---|
| 514967 | 7/1955 | Canada | 450/149 |

*Primary Examiner*—Edgar S. Burr

*Assistant Examiner*—Tonya Lamb

*Attorney, Agent, or Firm*—Harness, Dickey & Pierce

[57] ABSTRACT

A pelvic traction device inlcudes two detachably coupled belts that cooperate with each other to enable the device to be used over a wide range of patient sizes.

15 Claims, 4 Drawing Sheets

MEDICAL APPLIANCE HAVING AUXILIARY BELT TO PROVIDE ADJUSTABLE LENGTH RANGES

CROSS REFERENCE TO DISCLOSURE DOCUMENT

This application relates to Disclosure Document No. 167810 entitled "Multi-Size-Ranged Pelvic Traction Belt", filed 4-8-87.

BACKGROUND OF THE INVENTION

1. Technical Field

This invention relates to medical appliances and, more particularly, to pelvic traction devices.

2. Discussion

Pelvic traction devices generally take the form of belts which encircle a supine patient's pelvic area. a weight is attached to the belt to provide a static tractive force to the sacral lumbar spine. As will appear, the patent literature discloses a wide variety of different pelvic traction belt constructions.

Some of the prior art designs have been developed to fit a wide size range of patients. an obvious advantage of these so-called "universal" belts is that it reduces inventory requirements for hospitals and other institutions that use these devices. U.S. Pat. Nos. 3,572,327 to Beard; U.S. Pat. No. 3,797,483 to Feldman and U.S. Pat. No. 3,872,860 to Noblitt disclose these types of traction devices. One of the disadvantages of such belts is that their lengths are so long that it often becomes necessary to overlap portions of the belt when it comes to fitting small patients. The overlapping portion of the belt often reaches under the spine of the patient causing discomfort. Also, the end of the belt used for fastening purposes can become located underneath the patient thereby increasing the difficulty in applyiing and removing the belt. The overlapping problem also limits the practical maximum size range attainable by these single pelvic belts since making the belt longer will just increase the overlapping problem.

Tractive forces are applied to pelvic belts to rotate and flatten the sacral lumbar spine as disclosed in, for example, in U.S. Pat. No. 3,960,146 to Albrecht, by lifting and pulling the pelvis. The pelvis can be pulled at various angles as disclosed in U.S. Pat. No. 4,073,290 to Farrar Jr. The forces are generally applied by hanging weights attached to the belt. However, the force from the weights cannot deliver the desired static tractive force to the spine until the static resistance between the belt and the bed is overcome. In other words, the pelvic area needs to slide in the direction of the applied tractive force while the upper torso remains stationary in order to relieve the stress on the spine. The aforementioned U.S. Pat. No. 3,960,146 discloses a flattened tube of satin for the purpose of reducing sliding friction. However, it appears that the tube will not stay in position during use and can bunch up under the patient's back causing him discomfort. In addition, the tube is intended to slide in a back and forth direction only. The design does not appear to acccommodate patient movement from side to side in the bed which is sometimes necessary.

U.S. Pat. Nos. 3,452,747 to Varco and 3,522,802 to Morton mention that some of the known pelvic belts tend to concentrate the forces onto the soft tissues over the iliac crests which cause painful pressure points. It would be desirable to redistribute these forces more evenly over as much of the pelvic area as possible in order to reduce painful pressure on the iliac crests.

The aforementioned patents to Beard, Feldman and Noblitt require that the straps connected to the traction weight must be adjusted for each patient. While such adjustment can be accomplished, it is somewhat bothersome and not always easy to quickly perform. Consequently, it would be desirable to have a permanently affixed means for applying a tractive force to the patient.

SUMMARY OF THE INVENTION

Pursuant to the present invention, a pelvic traction device is provided that includes two belts that are detachable coupled together to provide a wide range of adjustments while avoiding at last some of the problems noted above. The main belt is defined by inner and outer major faces and has a given width and length. The auxiliary belt is likewise defined by inner and outer major faces and has substantially the same width as the main belt. The auxiliary belt is adapted to at least partially encircle the patient when the length of the main belt is insufficient to be used. The auxiliary belt is detachably connected to the main belt so that the auxiliary belt can be removed when the patient's torso in the pelvic area is small enough to be encircled by the main belt, yet the second belt can be used to provide an adjustable fit with larger patients.

BRIEF DESCRIPTION OF THE DRAWINGS

Various advantages of the present invention will become apparent to those skilled in the art upon reading the following specification and by reference to the drawings in which.

DESCRIPTION OF THE PREFERRED EMBODIMENT

It should be understood from the outset that the following description is not limited to limit the scope of the invention but instead is intended to provide a concise description of the best mode currently contemplated by the inventor for practicing his invention. Those skilled in the art will undoubtedly be in a position to modify the preferred embodiment without departing from the true scope of the invention after having the benefit of reading the following specification, drawings and claims.

Figures 2, 3, 4, 5:
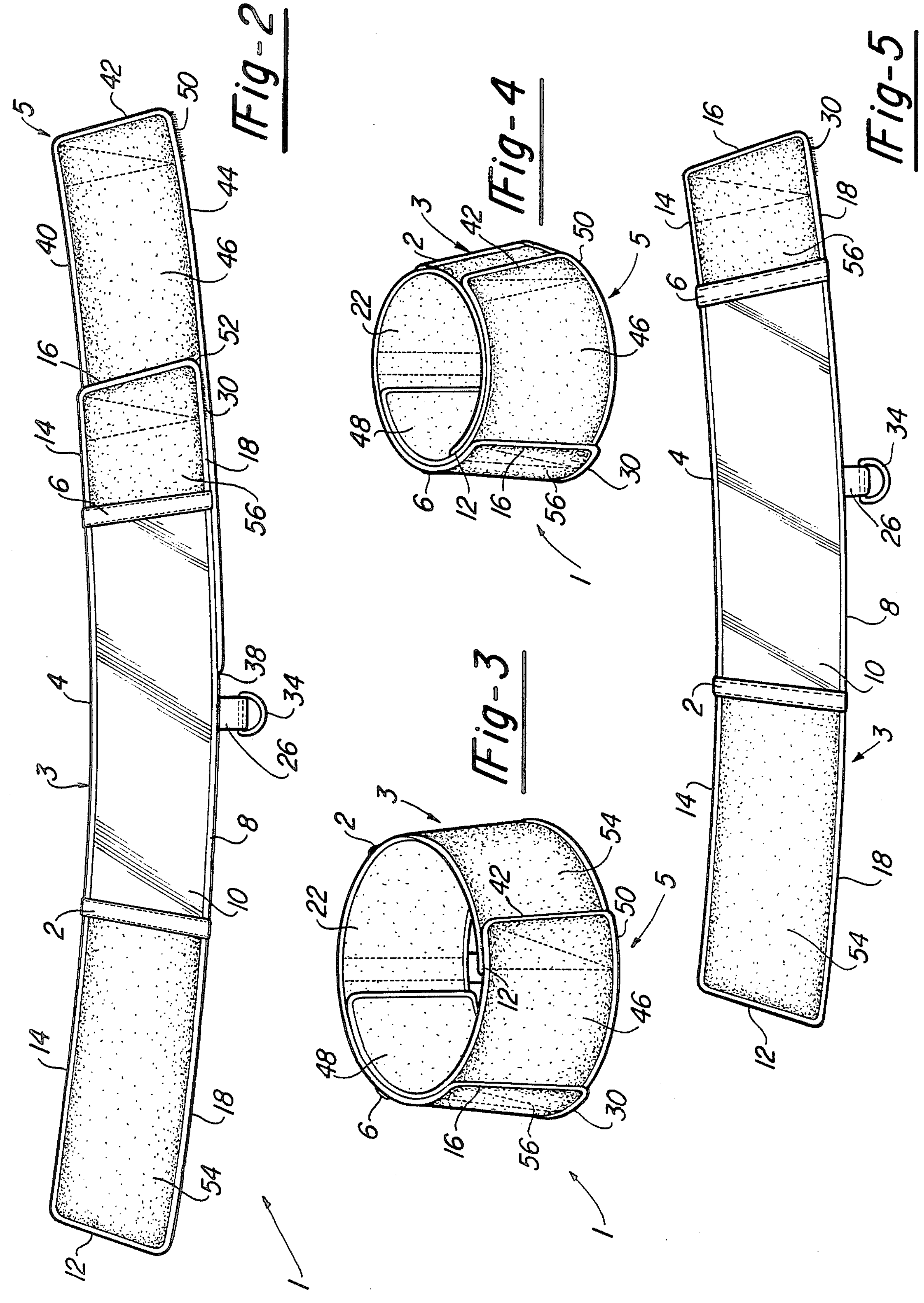
FIG. 2 is a plan view of the outer faces of the main and auxiliary belts, with the auxiliary belt being attached so as to provide the device with a range of adjustments for medium sizes.
FIG. 3 is a perspective view illustrating the belt of FIG. 2 encircled and attached to provide the maximum size limit for the middle size range.
FIG. 4 is a perspective view showing the belt of FIG. 2 encircled and attached so as to provide the minimum size limit of adjustment for the middle size range.
FIG. 5 is a plan view of the outside of the main belt lying flat.
Figures 6, 7, 8:
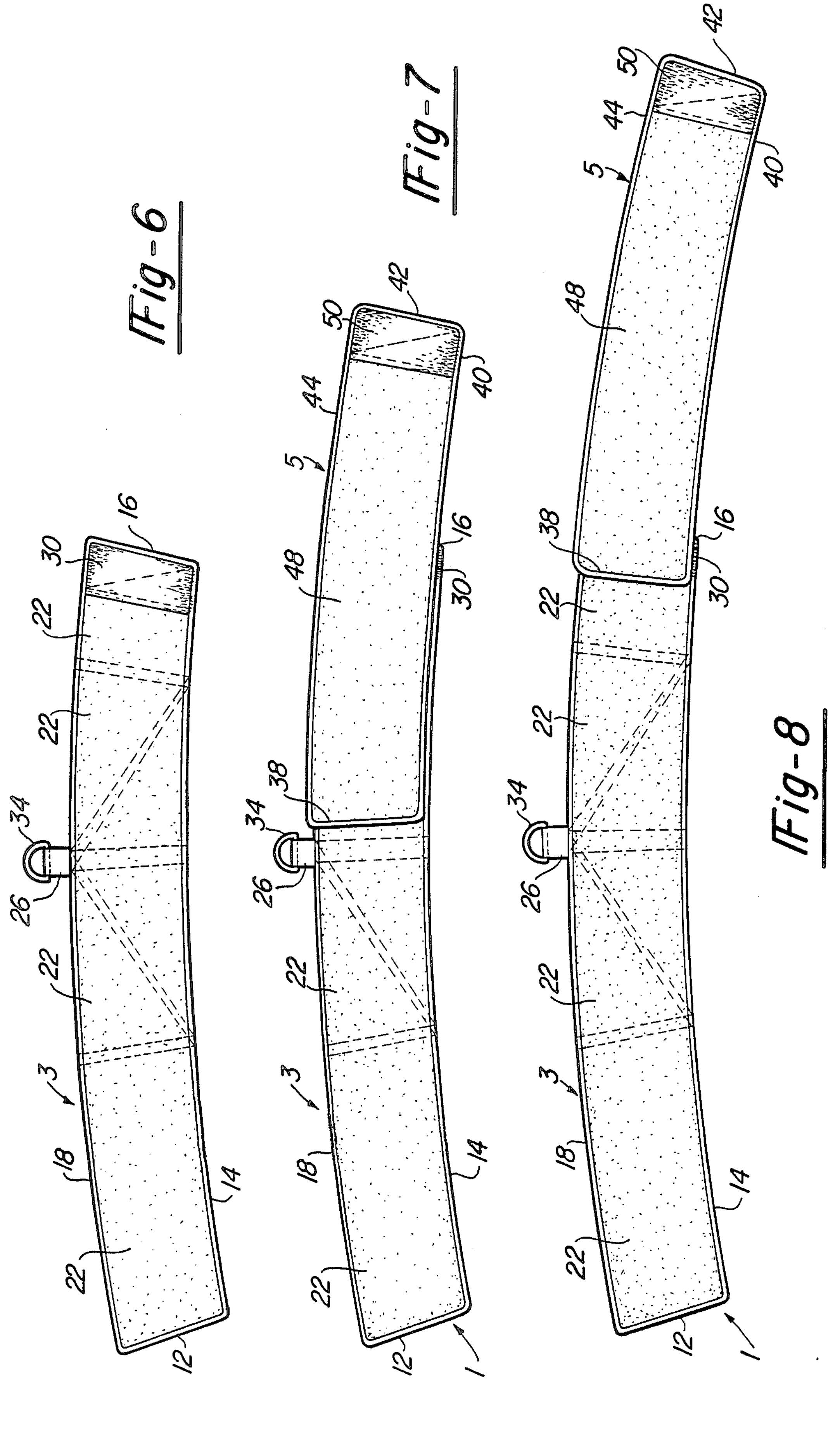
FIG. 6 is a plan view of the inside of the main belt lying flat.
FIG. 7 is a plan view of the inner face of the main and auxiliary belt, with the auxiliary belt being attached as in FIG. 2.
FIG. 8 is a view similar to FIG. 7 except that the auxiliary belt has been moved outwardly and attached to the main belt to provide the device with its largest range of adjustment.
Figure 9:
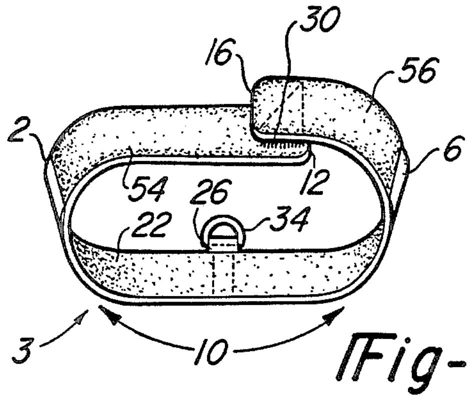
FIG. 9 is a perspective view of the main belt with its ends attached so as to provide the maximum limit for the small size range of the device.
Figure 10:
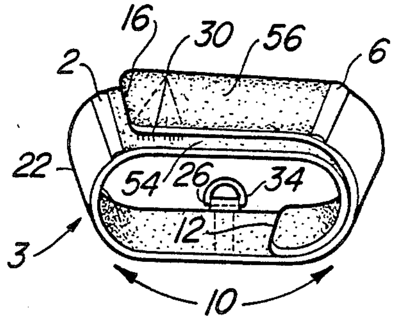
FIG. 10 is a view similar to FIG. 9 except that the main belt is attached so as to provide its maximum size limit.
Figure 12:
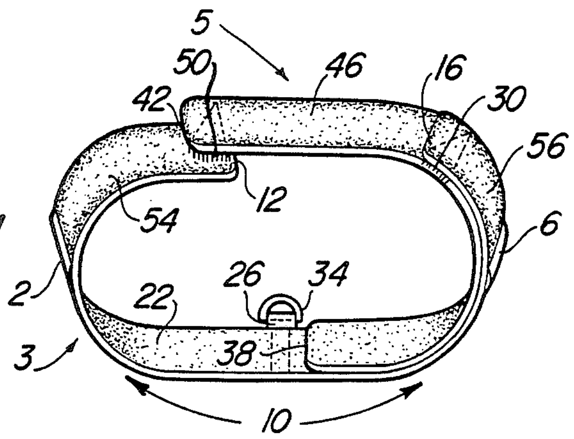
FIG. 12 is similar to FIG. 11 except that the ends are attached to provide the maximum size limit for the middle range of adjustment.
Figure 13:
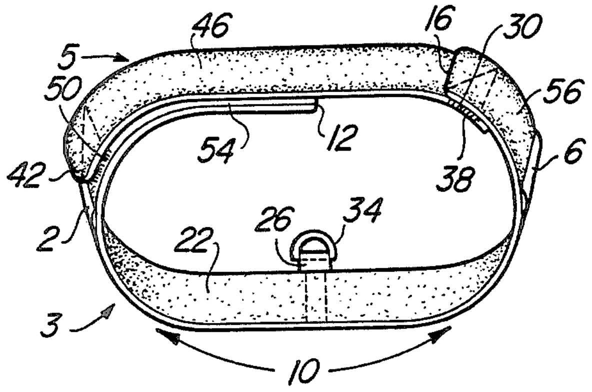
FIG. 13 is a view of the device with the auxiliary belt attached as in FIG. 8 and the ends thereof connected to provide the minimum size limit in the large range of adjustment.
Figure 14:
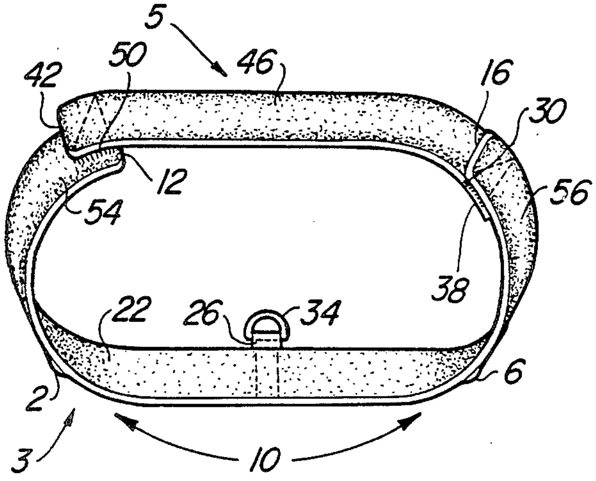
FIG. 14 is similar to FIG. 13 except that the ends are connected to provide the maximum limit for the large range of adjustment for the device.

As will appear, the preferred embodiment of the present invention provides a pelvic traction device 1 consisting of two somewhat similarly constructed belts: main belt 3 and auxiliary belt 5. By way of a nonlimiting example, main belt 3 is 41 inches in length and 10 inches wide whereas belt 5 is 25 inches in length and has substantially the same width as belt 3. When the belts are attached in the present position as shown in FIG. 2 (where end 16 of the main belt is attached to the auxiliary belt at 52) the device 1 provides a middle size range of adjustments designed to fit patient's torso pelvic area having circumferences of between 38–50 inches (see FIGS. 11 and 12). When the auxiliary belt 5 is attached to belt 3 as shown in FIG. 8, device 1 provides an adjustment of over the range of about 50–60 inches as illustrated in FIGS. 13 and 14, respectively. Belt 3 alone is designed to provide a small range of adjustments of between about 26–38 inches as shown in FIGS. 10 and 9, respectively. A study of FIGS. 9–14, in particular, illustrates that the belt 1 provides a wide range of adjustment yet there is a minimum amount of overlapping. In particular, there is no overlapping in the area where the patient's spine is adapted to rest, which is along the traction strap 26. As a result, the comfort of the patient is maximized.

Figure 1:
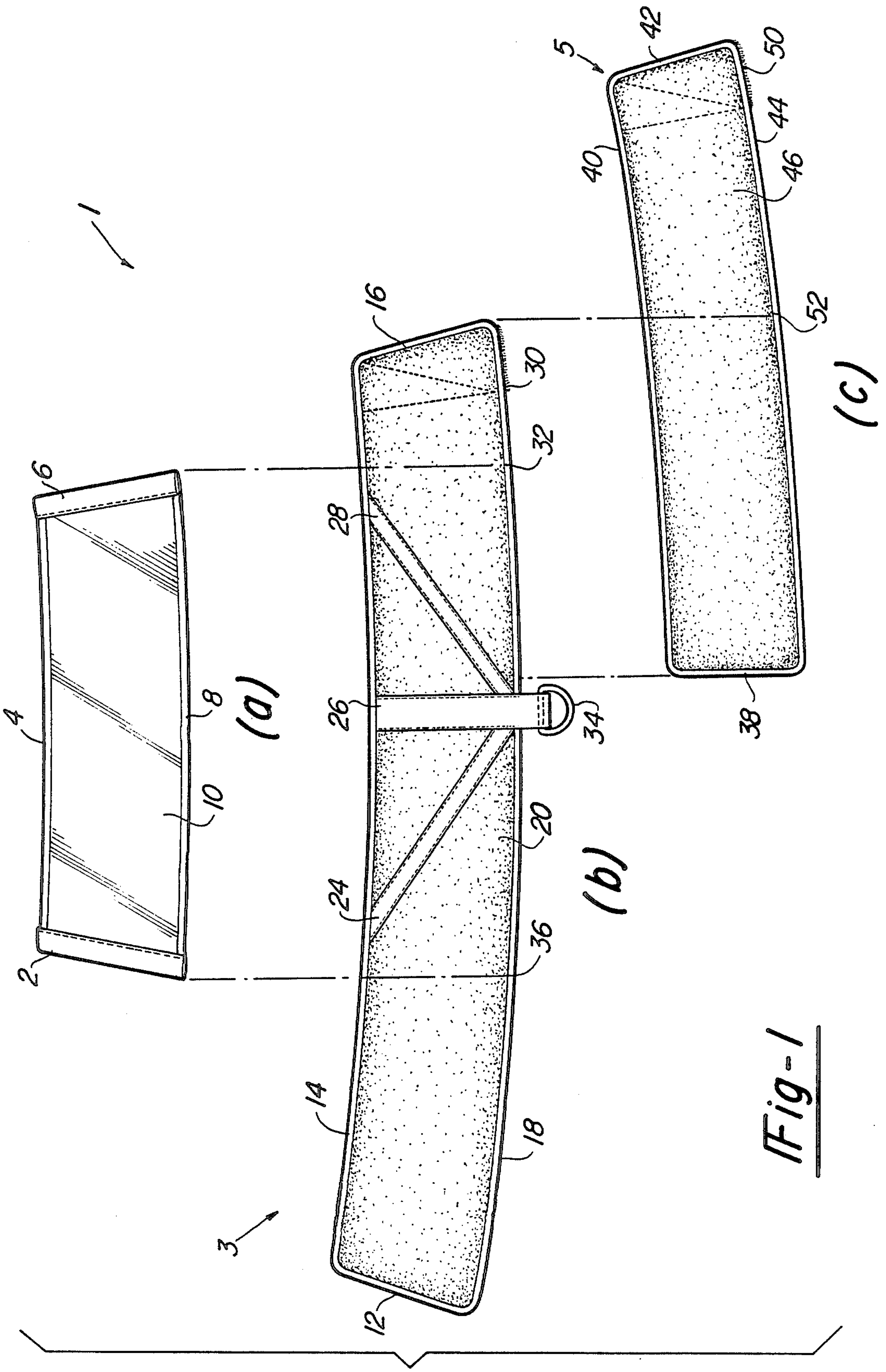
FIG. 1(*a–c*) is an exploded perspective view of a pelvic traction device made in accordance with teachings of the present invention.

The main belt 3 and auxiliary belt 5 are both constructed of bands of flexible material. The inner faces of both of the belts are constructed of foam padding. The outer faces of both belts are provided with pile fabric material that cooperates with hook material on the edges of the belts to form a fabric fastener of the "Velcro" brand type. The main belt 3 includes a sheet 10 of material having a low coefficient of friction, i.e., a slippery material. Preferably, sheet 10 is also waterproof. In the preferred embodiment sheet 10 is a piece of sail cloth made from nylon. As shown best in FIG. 1*a* sheet 10 is bound at top edge 4 and bottom edge 8. It is also provided with strap webbing 2 and 6 on its side edges. In FIG. 1*b* the outer face of belt 3 is shown with pile material 20. The inner face includes the foam padding 22 (see, e.g., FIGS. 3, 4 and 7). A traction strap is provided by way of webbing 26 attached to webbing 24 and 28, all radiating from the bottom 18 to the top 14 of the belt 3. The traction strap is permanently fixed to off center lengthwise on the belt 3 as shown in the drawings, with the strap 26 being provided with a ring 34 that is adapted to be connected to a weight to provide traction forces to the patient. The slippery sheet 10 is attached to the outer face of belt 3 off center and covering the webbing 24, 26 and 28. Sheet 10 is affixed, in this embodiment, by way of stitching located at 32 and 26 along the edges thereof.

As noted above, the outer face of auxiliary belt 5 (see, e.g. FIG. 1*c*) is provided with pile material 46 and an inside face of foam padding 48(see, e.g., FIGS. 3, 4 and 7). Belt 5 is provided with a bound top edge 40, a bound bottom edge 44 and bound side edges 38 and 42.

As best shown in FIGS. 6, 7 and 8 one end of main belt 3 includes a strip 30 of hook material that cooperates with the pile material to form a fabric fastener which is detachably connectable. Similarly, one edge of auxiliary belt 5 includes a strip 50 of hook material.

Figure 11:
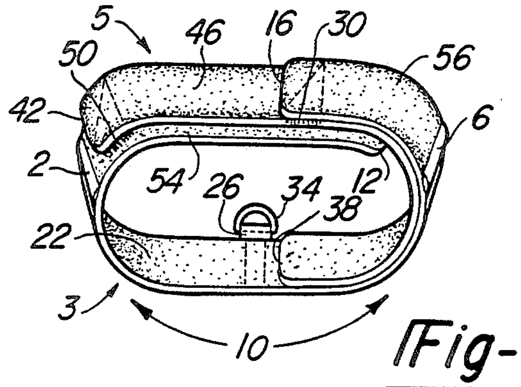
FIG. 11 is a a perspective view of the main/auxiliary belt combination where the auxiliary belt is attached to the main belt as in FIG. 2 and the ends are connected to provide the minimum size limit for the middle size range of adjustment.

As shown in FIG. 2 in the drawings, the main belt 3 includes two sections of different lengths located on either side of sheet 10. The pile material on the larger section 54 cooperates with hook strips 30 or 50 to fasten the device 1 about the torso of the patient in the pelvic area. As shown in FIGS. 9 and 10 the strip 30 on the main belt 3 can be adjusted over the length of section 54 to provide a range of sizes between about 26 and 38 inches in this embodiment. In FIGS. 11 and 12 the hook strip 50 on the auxiliary belt 5 cooperates with the pile material on section 54 to provide about a 38–50 inch range of adjustment. similarly, hook strip 50 provides a 50–60 range of adjustment as illustraed in FIGS. 13 and 14 when the auxiliary belt has been moved to the position shown in FIG. 8.

The pile section 54 is purposely limited in length to prevent excessive overlapping when the device 1 is used for smaller patients. The belt is designed so that the patient's spine should rest over the traction strap webbing 26. Referring especially to FIG. 5, the length of pile section 54 is less than the distance between strap 26 and the edge 16 of the opposite smaller section 56. In this example, sheet 10 is 20 inches in length, section 54 is 15 inches in length and section 56 is six inches in length. Thus, the 15 inch pile section 54 is less than ½ of the sheet length (10 inches) plus the six inch length of section 56 to prevent exceesive overlapping. In addition to avoiding the excessive overlapping problem, this construction provides quick and easy access to the ends 16 and 12 (FIGS. 9 and 10) of the device to permit the belt to be easily attached and removed from the patient.

The device 1 is designed so that it automatically informs the practitioner as to whether the belts are configured in the proper size range for the patient. The belts 3 and 5 are ordinarily attached as shown in FIG. 7 to define the middle size range (38–50 inches) for the device 1. The device is wrapped around the patient's pelvic torso area and if the Velcro strip 50 can be attached to section 54 as can be seen in FIG. 5 to provide the appropriate fit, then nothing else needs to be done. If the minimum limit setting shown in FIG. 11 is still too large to fit the patient, it indicates that the auxiliary belt 5 must be removed. The practitioner will know that the present configuration is too large because the Velcro strip 50 will not attach to the slippery material of sheet 10 once the strip 50 extends beyond edge 2. The removal of belt 5 creates the small size range configuration (26–38 inches) shown in FIG. 6 which fits patients within the minimum and maximum limits shown in FIGS. 10 and 9, respectively. On the other hand, if the configuration shown in FIG. 12 is still too small for the patient, the practitioner "knows" that it is necessary to move the auxiliary belt 5 to the position shown in FIG. 8 thereby providing device 1 with its large range of adjustment (50–60 inches). Again, FIG. 13 shows the minimum limit whereas FIG. 14 shows the maximum limit for this large size range.

One of the features of this invention is that the minimum size limit of the middle size range (FIG. 11) is about the same as the maximum size limit of the small size range (FIG. 9) and the maximum size limit of the middle size range (FIG. 12) is about the same as the minimum size limit of the large size range (FIG. 13). Thus, the device 1 permits a plurality of patient sizes to be fitted in uninterrupted progression through all the size ranges. In other words, the length of the main belt smaller section 56 and the length of the auxiliary belt 5 are chosen so that the following diameters of device 1 are substantially the same: (a) that of the main/auxiliary belt combination when the auxiliary belt is connected so that its edge 38 is adjacent the strap 26 and the hook strip 50 on the other edge 42 is adjacent an edge 2 of the sheet 10(FIG. 11); and (b) that of the main belt 3 only when the hook strip 30 is adjacent the edge 12 of the larger section 54 (FIG. 9). In addition, the following configurations also define diameters which are about the same: (a) the main/auxiliary belt combination when the auxiliary belt 5 is connected so that its edge 38 is adjacent strap 26 and the strip 50 is adjacent the edge 12 of the larger section 54 (FIG. 12); and (b) the main/auxiliary belt combination when auxiliary belt 5 is connected so that its edge 38 is adjacent the hook strip 30 on the main belt smaller section 56 and the hook strip 50 on the auxiliary belt 5 is adjacent the edge 2 of sheet 10 (FIG. 13). In summary, the diameters defined by the device configurations in FIGS. 9 and 11 are the same, just as the diameters defined by the device configurations in FIGS. 12 and 13.

The sheet 10 of slippery material is of adequate size to cover the area of contact between the device 1 and the bed or supporting surface upon which the patient lies. The sheet 10 possesses a low cofficient of static friction, thereby reducing static resistance so that the amount of uncomfortable static tractive forces applied to the patient are minimized. The sheet 10 also possesses a low coefficient of sliding friction thereby reducing sliding resistance so that the encircled pelvic torso area can slide in any direction to a new position with less trauma to the patient than lifting or rolling him. It is important to note that the patient can more easily shift from side to side in the bed as well as longitudinally therein as a result of the device's construction. Preferably, the sheet material 10 is also waterproof thereby protecting the belt and patient from moisture when hot packs or the like are applied to the patient's back as is often the case during treatment.

The inside foam padding of belts 3 and 5 are of a sufficient thickness to pad the patient's soft tissues at pressure points about the pelvic area thereby increasing patient comfort. the foam padding possesses a high coefficient of static friction thereby increasing static resistnce enabling skin traction to be utilized to distribute some of the tractive forces onto the skin areas away from the pressure points. This creates a more evenly balanced pressure on the soft tissues of the patient's pelvic area.

The single action traction strap 26 and hook 34 acts as an alignment guide as noted above for placing the device 1 onto the patient. It also is designed to deliver a low angle pulling tractive force which is generally more efficient than a high angle lifting, pulling tractive force. This reduces the amount of static tractive forces applied to the patient thereby also increasing patient comfort.

As noted above, this invention has been described in connection with a particular example thereof but no limitation is intended thereby except as defined in the following claims.

What is claimed is:

1. A medical appliance device for use with patients of various sizes, said device comprising:
   - a main belt defined by inner and outer major faces, the main belt having a given width and length, the main belt having a first end section, a second end section;
   - an auxiliary belt defined by inner and outer major faces, the auxiliary belt having substantially the same width as the main belt;
   - fastening means for reusably detachably connecting the main and auxiliary belts; and
   - the main and auxiliary belts being sufficiently dimensioned so as to provide three continuous size ranges: a middle size range when the auxiliary belt is connected in a preset position lengthwise overlapping the second end section and at least partially overlapping the center section, a small size range when the auxiliary belt is removed, and a large size range when the auxiliary belt is moved from said preset position and attached to said main belt so that an end of the auxiliary belt is connected adjacent to the outer end of the second section of the main belt, wherein the largest size of the small range is substantially the same as the smallest size of the middle range and the largest size of the middle range is substantially the same as the smallest size of the large range to thereby provide a continuum of sizes.

2. The device of claim 1 wherein the outer face of the main belt includes a substantially smooth sheet of low coefficent of frictional material.

3. The device of claim 2 wherein said sheet extends the width of the main belt and is offset towards one end thereof thereby dividing the outer face into first and second end sections, the length of the first section being larger than the length of the second section.

4. The device of claim 3 which further comprises:
   - traction strap means, extending transversely across the middle of said sheet, for providing connection to a weight for applying tractive forces to the patient wearing the belt.

5. The device of claim 4 wherein the length of the first section of the main belt is less than the distance between the traction strap means and a slide edge of the second section to thereby avoid excessive overlapping of the first section when the device is used on a patient of relatively small size, the strap providing a visual guide for positioning the patient's spine so that it lies on the strap.

6. The device of claim 5 wherein:
   - the outer face of the first section is made of pile material;
   - the inner face of the second section includes a strip of hook material along an outer side edge thereof; said strip cooperating with the pile material on the first section to fasten the main belt to patients having said small range of waist sizes; and an outer face of the auxiliary belt being made of pile material whereby said strip can alternatively cooperate therewith to form said fasteneing means for detachably coupling the auxiliary belt to the main belt to provide said middle and large size ranges of adjustments.

7. The device of claim 6 wherein the inner faces of the main and auxiliary belts are made of a high coefficient of friction material thereby enabling skin traction to be utilized to distribute tractive forces onto skin areas thereby providing a more evenly balanced pressure on the patient's tissues.

8. The device of claim 7 wherein said inner faces of the main and auxiliary belts are made of foam padding.

9. The device of claim 6 wherein the inner face of the auxiliary belt has a strip along one side edge thereof made of hook material for cooperating with the pile material on the first section of the main belt to enclose the device around the patient when the auxiliary belt is used.

10. The device of claim 9 wherein the length of the main belt second section and that of the auxiliary belt are chosen so that the following diameters are substantially the same:

(a) that of the main belt only when its hook strip is adjacent the outer edge of the first section thereof; and (b) that of the main/auxiliary belt combination when the auxiliary belt is connected so that its other side edge is adjacent the traction strap means and its hook strip on the one edge is adjacent an edge of the sheet.

11. The device of claim 10 wherein the length of the main belt second section and that of the auxiliary belt are chosen so that the following diameters are substantially the same:

(a) that of the main/auxiliary belt combination when the auxiliary belt is connected so that its other edge is adjacent the traction strap and its hook strip on the one edge is adjacent the outer edge ofthe first section; and (b) that of the main/auxiliary belt combination when the auxiliary belt is connected so that its other edge is adjacent the hook strip on the second section of the main belt and the hook strip on the one opposite edge of the auxiliary belt is adjacent the edge of the sheet.

12. A pelvic traction device comprising:

a main belt of flexible material having inner and outer major faces, a given width and a given length between two outer side edges thereof, the outer face of the main belt having a sheet of smooth material affixed thereto extending across the width of the belt and being located offset with respect to the length of the belt thereby dividing it into a larger section and a smaller section, the outer faces of the larger and smaller sections being made of pile material; a traction strap extending across the width of the belt and being centrally located between opposing lengthwise side edges of the sheet; the majority of the inner face of the main belt including a strip of hook material on the outer edge of said smaller section on the inner face thereof; and an auxiliary belt having inner and outer major faces, the auxiliary belt having substantially the same width as said main belt and a given length defined between two side edges thereof, the outer face of the auxiliary belt being made of pile material, the majority of the inner face of the auxiliary belt being made of the same material as the inner face of said main belt; and said auxiliary belt having a strip of hook material on its inner face along one of the side edges thereof; wherein said strips of hook material are alternatively attachable to said pile material of said main belt to provide a plurality of sizes.

13. The pelvic traction device of claim 12 wherein the length of the larger section is less than the distance between said traction strap and the hook strip on the smaller section.

14. The device of claim 12 wherein the total length of the main belt is about 41 inches, the length of the sheet is about 20 inches, the length of the larger section is about 15 inches and the length of the smaller section is about 6 inches.

15. The device of claim 14 wherein the length of the auxiliary belt is about 25 inches.

* * * * *

UNITED STATES PATENT AND TRADEMARK OFFICE

CERTIFICATE OF CORRECTION

PATENT NO. : 4,747,399

DATED : May 31, 1988

INVENTOR(S) : Roger R. Glomstead

It is certified that error appears in the above-identified patent and that said Letters Patent is hereby corrected as shown below:

Col. 1, line 18, "a" (second occurrence) should be --A--.

Col. 1, line 24, "an" should be --An--.

Col. 1, line 37, "applyiing" should be --applying--.

Col. 1, line 67, insert "can" before --cause--.

Col. 2, line 16, "last" should be --least--.

Col. 2, line 53, "face" should be --faces--.

Col. 2, line 64, "maximum" should be --minimum--.

Col. 3, line 17, "limited" should be --intended--.

Col. 3, line 33, "present" should be --preset--.

Col. 4, line 8, "26" should be --36--.

UNITED STATES PATENT AND TRADEMARK OFFICE
CERTIFICATE OF CORRECTION

PATENT NO. : 4,747,399

DATED : May 31, 1988

INVENTOR(S) : Roger R. Glomstead

It is certified that error appears in the above-identified patent and that said Letters Patent is hereby corrected as shown below:

Col. 5, line 44, "cofficient" should be --coefficient--.

Col. 5, line 62, "the" should be --The--.

Col. 5, line 64, "resistnce" should be --resistance--.

Col. 6, line 18, insert --and a center section-- after "section" (3rd occurrence).

Col. 6, line 43, "frictional" should be --of friction--.

Col. 6, line 57, "slide" should be --side--.

Col. 7, line 4, "alternatively" should be --alternately--.

Col. 7, line 5, "fasteneing" should be --fastening--.

Col. 7, line 42, "ofthe" should be --of the--.

UNITED STATES PATENT AND TRADEMARK OFFICE

CERTIFICATE OF CORRECTION

PATENT NO. : 4,747,399

DATED : May 31, 1988

INVENTOR(S) : Roger R. Glomstead

It is certified that error appears in the above-identified patent and that said Letters Patent is hereby corrected as shown below:

Col. 8, line 18, insert --being made of foam padding material; and the main belt-- after "belt".

On the Title Page under References Cited, please include the following U.S. Patents:

| | | | |
|---|---|---|---|
| --3,452,747 | 07/01/69 | S. Varco | 128/75 |
| 3,522,802 | 08/04/70 | W. Morton | 128/75 |
| 3,561,434 | 02/09/71 | R. Kilbey | 128/75 |
| 3,572,327 | 03/23/71 | L. Beard et al | 128/75 |
| 3,587,570 | 06/28/71 | R. Kilbey | 128/75 |
| 3,797,483 | 03/19/74 | I. Feldman | 128/75 |
| 3,872,860 | 03/25/75 | N. Noblitt | 128/75 |
| 3,960,146 | 06/01/76 | D. Albrecht | 128/75 |
| 4,073,290 | 02/14/78 | E. Farrar, Jr. | 128/75--. |

UNITED STATES PATENT AND TRADEMARK OFFICE
CERTIFICATE OF CORRECTION

PATENT NO. : 4,747,399

DATED : May 31, 1988

INVENTOR(S) : Roger R. Glomstead

It is certified that error appears in the above-identified patent and that said Letters Patent is hereby corrected as shown below:

On the Title Page under References cited, please include the following under Other Documents:

--Richards' Brochure, "Traction Equipment" Section III, pages 180, 181.
United Medical Brochure, "Traction Accessories", pages 36, 37.
Zimmer Brochure, "Pelvic Traction Belts", 1975.
Zimmer Brochure, "Pelvic Belts, Head Halters, Cotrel Dynamic Traction", pg. 49-56.
DePuy Brochure, "BB Traction", pages 23-25.
Biomet Brochure, "Traction Systems and Accessories", pages Q3-Q6.--

Signed and Sealed this

Sixteenth Day of May, 1989

*Attest:*

DONALD J. QUIGG

*Attesting Officer* *Commissioner of Patents and Trademarks*